(12) United States Patent
Yoshimura (10) Patent No.: US 10,145,288 B2
(45) Date of Patent: Dec. 4, 2018

(54) EXHAUST GAS MEASUREMENT APPARATUS, PROGRAM TO BE INSTALLED THEREIN, AND CONTROL METHOD THEREOF

(71) Applicant: HORIBA, Ltd., Kyoto (JP)

(72) Inventor: Tomoshi Yoshimura, Kyoto (JP)

(73) Assignee: Horiba, Ltd., Kyoto (JP)

( * ) Notice: Subject to any disclaimer, the term of this patent is extended or adjusted under 35 U.S.C. 154(b) by 100 days.

(21) Appl. No.: 15/364,930

(22) Filed: Nov. 30, 2016

(65) Prior Publication Data

US 2017/0167348 A1 Jun. 15, 2017

(30) Foreign Application Priority Data

Dec. 10, 2015 (JP) ................................. 2015-241542

(51) Int. Cl.
*G01M 15/10* (2006.01)
*F01N 11/00* (2006.01)
(Continued)

(52) U.S. Cl.
CPC ................ *F01N 11/00* (2013.01); *F01N 3/00* (2013.01); *G01M 15/102* (2013.01);
(Continued)

(58) Field of Classification Search
USPC .............................. 73/114.71, 114.72, 114.73
See application file for complete search history.

(56) References Cited

U.S. PATENT DOCUMENTS

2014/0251031 A1* 9/2014 Kumagai ............. G01N 1/2252
73/863.41
2014/0290336 A1* 10/2014 Miyai .................... G01N 19/10
73/29.01

(Continued)

FOREIGN PATENT DOCUMENTS

JP 2004-100648 A 4/2004
JP 2010-139340 A 6/2010
(Continued)

OTHER PUBLICATIONS

European Search Report for Application No. EP 16201171.2, dated Apr. 28, 2017, 8 pages.

*Primary Examiner* — Eric S McCall
(74) *Attorney, Agent, or Firm* — Brooks Kushman P.C.

(57) ABSTRACT

In order to provide an exhaust gas measurement apparatus having a simpler configuration capable measuring a concentration of a predetermined component contained in exhaust gas under various situations without deteriorating a measurement accuracy, there is provided a sampling mechanism that can select any one of two states, i.e., a first operation mode for outputting the sampled exhaust gas without dilution and a second operation mode for outputting the sampling exhaust gas mixed with dilution gas. In a situation where the sampling mechanism is operating in the first operation mode, in the case where the concentration of the predetermined component measured by a measurement apparatus body exceeds a predetermined first threshold value, the sampling mechanism is controlled such that the first operation mode thereof is changed to the second operation mode.

4 Claims, 7 Drawing Sheets

(51) Int. Cl.
*F01N 3/00* (2006.01)
*G01N 33/00* (2006.01)
*G01N 1/22* (2006.01)

(52) U.S. Cl.
CPC ......... G01N 1/2252 (2013.01); G01N 33/004 (2013.01); *G01N 2001/2255* (2013.01)

(56) References Cited

U.S. PATENT DOCUMENTS

| | | | | |
|---|---|---|---|---|
| 2014/0338540 | A1* | 11/2014 | Yoshimura | G01N 1/2252 96/413 |
| 2016/0273438 | A1* | 9/2016 | Otsuki | F01N 11/007 |
| 2017/0167351 | A1* | 6/2017 | Kumagai | F01N 11/007 |
| 2017/0168033 | A1* | 6/2017 | Yoshimura | F01N 3/033 |

FOREIGN PATENT DOCUMENTS

| | | |
|---|---|---|
| JP | 2014-174055 A | 9/2014 |
| WO | 2014202771 A2 | 12/2014 |

* cited by examiner

EXHAUST GAS MEASUREMENT APPARATUS, PROGRAM TO BE INSTALLED THEREIN, AND CONTROL METHOD THEREOF

CROSS-REFERENCE TO RELATED APPLICATION

This application claims priority to JP Application No. 2015-241542, filed Dec. 10, 2015, the disclosure of which is incorporated in its entirety by reference herein.

TECHNICAL FIELD

The present invention relates to an exhaust gas measurement apparatus and the like for measuring a concentration of such as a CO component (also, simply referred to as "CO concentration" hereinafter) contained in exhaust gas discharged from an internal combustion engine and the like.

BACKGROUND ART

In this type of the exhaust gas measurement apparatus, as disclosed in Patent Literature 1, concentrations of various components contained in the exhaust gas discharged from an internal combustion engine are measured.

Especially, a CO concentration is varied largely in a short time in a range from a several ppm order to a percentage (%) order according to an operating condition of an engine and a warming-up state of a catalyst.

For example, in a state that a large amount of fuel is supplied and a catalyst is not yet sufficiently warmed, at a time of initial operation of the engine or the like, since there occurs an incomplete combustion and a catalytic function is not sufficiently exerted, CO gas produced by such as an incomplete combustion is discharged from a vehicle tailpipe of a vehicle without being oxidized to be $CO_2$ by the catalyst. Therefore, the CO concentration at this time is extremely high. Meanwhile, in the case where the catalyst is warmed up, the CO component is almost oxidized to be $CO_2$ by the catalyst and therefore the concentration of the CO component contained in the exhaust gas is reduced to be a few ppm order.

In this way, since a difference between a high concentration and a lower concentration of the CO component is large, the CO concentration has been conventionally measured by providing two types of CO concentration meters having, for example, different measurement ranges.

However, since it is necessary to use two types of the CO concentration meters, there is a problem that a maintenance cost and an initial investment cost are increased. Further, also in measurement accuracy, a correlation at a timing of switching between the two CO concentration meters becomes a problem of measurement accuracy in some cases.

Similar problems may also arise in measuring concentrations of the other components (for example, THC and the like) contained in the exhaust gas.

CITATION LIST

Patent Literature

Patent Literature 1: JP2014-174055A

SUMMARY OF INVENTION

Technical Problem

Therefore, the present invention has been made in consideration of the above problems, and an essential object thereof is to provide an exhaust gas measurement apparatus capable of measuring a concentration of a predetermined component contained in exhaust gas under various situations with a simpler configuration without deteriorating a measurement accuracy.

Solution to Problem

That is, in one aspect of the present invention, an exhaust gas measurement apparatus is characterized by comprising following components (1) to (3):

(1) a sampling mechanism adapted to sample exhaust gas discharged from an internal combustion engine and to be able to select any one of two states of a first operation mode and a second operation mode, specifically, in the first operation mode, the sampled exhaust gas being outputted without dilution or the sampled exhaust gas mixed with dilution gas of a predetermined ratio or less being outputted, and in the second operation mode, the sampling exhaust gas mixed with dilution gas beyond a predetermined ratio being outputted;

(2) a measurement apparatus body adapted to introduce the gas outputted from the sampling mechanism and adapted to measure a concentration of a predetermined component contained in the gas; and (3) a control mechanism adapted to control the sampling mechanism, and in the case where the concentration measured by the measurement apparatus body exceeds a predetermined first threshold value in a situation that the sampling mechanism is operating in the first operation mode, the control mechanism being adapted to control the sampling mechanism so as to change the first operation mode to the second operation mode.

With this configuration, even if there may be a case where a concentration of a predetermined component contained in the sampling exhaust gas is increased due to such as a change of the state of the internal combustion engine and exceeds a measurable range of the measurement apparatus body and, for example, it will be unmeasurable directly, by switching the operation mode of the sampling mechanism to the second operation mode, the sampling exhaust gas is diluted and the concentration of the predetermined component can be decreased to a measurable concentration range of the measurement apparatus body. Thus, the concentration of the predetermined component can be measured by a single measurement apparatus body. It is needless to say that, in the case of diluting the sampling exhaust gas, it is necessary to calculate the concentration of the predetermined component contained in the exhaust gas in consideration of a dilution ratio to the measurement concentration obtained by the measurement apparatus body. However, since it is not necessary to provide a plurality of types of measurement apparatus main bodies (for example, a CO concentration meter) having different measurable ranges as is required in the conventional case, the configuration of the exhaust gas measurement apparatus can be simplified. Moreover, there is no correlation problem which has been caused due to switching of a plurality of measurement apparatus main bodies as in the conventional case, and not only the measurement accuracy can be ensured but also it becomes possible to contribute to improvement of the measurement accuracy.

In order to be able to deal with also in the case where the concentration of the predetermined component contained in the sampling exhaust gas is decreased from a high state, it is preferable that the control mechanism is configured as follows.

In other words, it is preferable that, in the case where the concentration measured by the measurement apparatus body is below a predetermined second threshold value in a situation that the sampling mechanism is operating in the second operation mode, the control mechanism is adapted to control the sampling mechanism so as to change the second operation mode to the first operation mode.

As a specific embodiment, in the second operation mode, it is sufficient to allow the dilution gas to be added and mixed to the sampling exhaust gas flowing in the first operation mode. However, in this configuration, the flow rate of the gas to be introduced to the measurement apparatus body in the second operation mode becomes larger by a dilution gas amount, compared to that in the first operation mode. Therefore, there may arise a significant difference between the flow rates of the gas introduced to the measurement apparatus body in the first operation mode and in the second operation mode, and it is liable to cause a measurement error due to the above fact.

Therefore, in order to reduce the difference between the flow rates of the gas introduced to the measurement apparatus body in the first operation mode and in the second operation mode and relieve the above problem, it is preferred that, the flow rates of the sampling exhaust gas to be introduced to the measurement apparatus body are set to be different from each other between in the first operation mode and in the second operation mode, and the flow rate of the sampling exhaust gas in the first operation mode is set to be larger than that in the second operation mode.

Advantageous Effects of Invention

According to the exhaust gas measurement apparatus according to the present invention, since the concentration of the predetermined component can be measured by a single measurement apparatus body even in the case where the concentration of the predetermined component contained in the exhaust gas is largely changed, the configuration of the exhaust gas measurement apparatus can be simplified and further it becomes possible to ensure the measurement accuracy.

DESCRIPTION OF EMBODIMENTS

The following describes various embodiments of the present invention referring to the accompanying drawings.

First Embodiment

Figure 1:
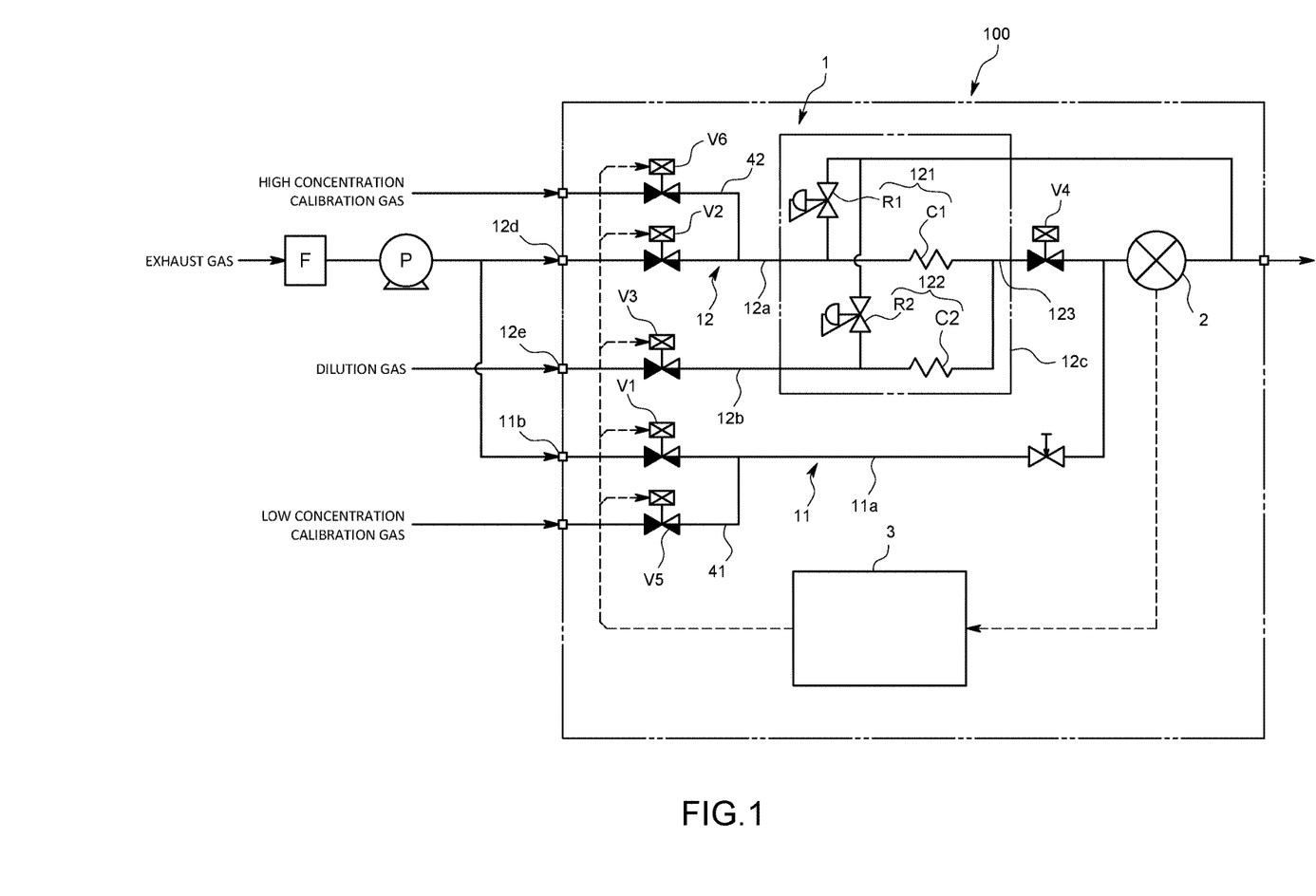
FIG. 1 is a fluid circuit diagram showing an entire exhaust gas measurement apparatus in a first embodiment of the present embodiment.

As shown in FIG. 1, an exhaust gas measurement apparatus 100 according to the present embodiment includes: a sampling mechanism 1 for sampling a partial portion of exhaust gas discharged from an internal combustion engine (not shown); a measurement apparatus body 2 which is connected to the sampling mechanism 1 and measures a concentration of a predetermined component (CO in this case) contained in the gas outputted from the sampling mechanism 1; and a control mechanism 3 for controlling the sampling mechanism 1. Each part is described as below.

The sampling mechanism 1 is adapted to be able to select any one of two operation modes: a first operation mode in which an internal flow channel thereof is switched and the sampled exhaust gas (also, referred to as "sampling exhaust gas" hereinafter) is outputted directly; and a second operation mode in which the sampling exhaust gas is mixed with a predetermined ratio of dilution gas and the resultant mixture gas is outputted. Note that the sampling exhaust gas mentioned here may be raw gas outputted from the internal combustion engine or diluted exhaust gas diluted by such as dilution tunnel CVS. The following describes more specifically.

The sampling mechanism 1 includes a first flow channel system 11 in which the sampling exhaust gas flows in the first operation mode and a second flow channel system 12 in which the sampling exhaust gas flows in the second operation mode.

The first flow channel system 11 includes a first exhaust gas flow channel 11a to which the sampling exhaust gas is introduced. The first exhaust gas flow channel 11a is provided with a first exhaust gas introduction port 11b at its starting end which is, for example, connected to an external pump P. As shown in FIG. 1, the first exhaust gas flow channel 11a is adapted to sample the exhaust gas sucked by the external pump P and guide the sampling exhaust gas directly to the measurement apparatus body 2 which is connected to a terminal end of the first exhaust gas flow channel 11a. In FIG. 1, reference numeral V1 provided at a starting end portion of the first exhaust gas flow channel 11a denotes a first valve for opening and closing the first exhaust gas flow channel 11a.

The second flow channel system 12 includes: a second exhaust gas flow channel 12a to which the sampling gas is introduced; a dilution gas flow channel 12b to which the dilution gas (for example, N2) is introduced; and a dilution portion 12c which is adapted to mix the sampling exhaust gas flowing through the second exhaust gas flow channel 12a and the dilution gas flowing through the dilution gas flow channel 12b at a predetermined constant ratio and guide the resultant mixture gas to the measurement apparatus body 2.

The second exhaust gas flow channel 12a is provided with a second exhaust gas introduction port 12d at its starting end which is connected to the external pump. As shown in FIG. 1, the second exhaust gas flow channel 12a is adapted to sample the exhaust gas sucked by the external pump P. In FIG. 1, reference numeral V2 provided at a starting end portion of the second exhaust gas flow channel 12a denotes a second valve for opening and closing the second exhaust gas flow channel 12a.

The dilution gas flow channel 12b is provided with a dilution gas introduction port 12e at its starting end which is, for example, connected to a dilution gas source such as a gas bomb (not shown) and adapted to introduce the dilution gas supplied from the dilution gas source. In FIG. 1, reference numeral V3 provided at a starting end portion of the dilution gas flow channel 12b denotes a third valve for opening and closing the dilution gas flow channel 12b.

The dilution portion 12c includes: an exhaust gas acquisition part 121 and a dilution gas acquisition part 122 for acquiring the sampling exhaust gas flowing through the second exhaust gas flow channel 12a and the dilution gas flowing through the dilution gas flow channel 12b, respectively, so as to be at the predetermined constant ratio therebetween; and a mixing part 123 for mixing the exhaust gas and the dilution gas outputted from the exhaust gas acquisition part 121 and the dilution gas acquisition part 122, respectively.

The exhaust gas acquisition part 121 includes: a first pressure regulating valve R1 connected to the second exhaust gas flow channel 12a; and a first fluid resistance element C1 such as a capillary connected to a downstream side of the first pressure regulating valve R1 in the second exhaust gas flow channel 12a. The first pressure regulating valve R1 is adapted to keep the internal pressure of the second exhaust gas flow channel 12a to be a predetermined constant pressure by discharging a partial portion of the sampling exhaust gas from an escape port thereof. The first fluid resistance element C1 is adapted to keep the flow rate of the exhaust gas flowing through the first fluid resistance element C1, i.e., the flow rate of the sampling exhaust gas outputted from the exhaust gas acquisition part 121 to be a predetermined constant value by connecting the first fluid resistance element C1 to the second exhaust gas flow channel 12a kept at the predetermined constant pressure.

The dilution gas acquisition part 122 includes: a second pressure regulating valve R2 having an input port connected to the terminal end of the dilution gas flow channel 12b; and a second fluid resistance element C2 such as a capillary connected to an output port of the second pressure regulating valve R2. The second pressure regulating valve R2 is adapted to keep the output port thereof to be at a predetermined constant pressure by discharging a partial portion of the dilution gas from an escape port thereof. The second fluid resistance element C2 is adapted to keep the flow rate of the dilution gas flowing through the second fluid resistance element C2, i.e., the flow rate of the dilution gas outputted from the dilution gas acquisition part 122 to be a predetermined constant value by connecting the second fluid resistance element C2 to the output port kept at the predetermined constant pressure.

The mixing part 123 is adapted to introduce the sampling exhaust gas and the dilution gas respectively outputted from the exhaust gas acquisition part 121 and the dilution gas acquisition part 122 at a constant ratio and at a constant flow rate and mix these outputted sampling exhaust gas and dilution gas and then guide the resultant mixture gas to the measurement apparatus body 2. Here, a pipe member commonly connected to the output ports of the exhaust gas acquisition part 121 and the dilution gas acquisition part 122 plays the function thereof.

In this embodiment, the ratio of the sampling exhaust gas and the dilution gas in the mixture gas that is outputted from the second flow channel system 12 is approximately 1:19. This dilution ratio (about 20 times) is determined by a measurement dynamic range (a ratio of the measurement maximum value to the measurement minimum value) and a resolution of the measurement apparatus body 2. In specific, the dilution ratio is set to be in a degree of 1/5 to 1/500, preferably 1/10 to 1/100 of the dynamic range. Meanwhile, the flow rate of the mixture gas is set to be substantially equal to the flow rate of the sampling exhaust gas outputted from the first flow channel system 11.

The measurement apparatus body 2 is, for example, absorption photometer typed one, and, although not shown, it is adapted to guide light emitted from a light source to a light-transmission cell while being filled with a measurement target gas and then calculate a concentration of a CO component contained in the measurement target gas from an absorbance of a predetermined wavelength of the light. The measurement range of the measurement apparatus body 2 is determined by an optical path of the cell, and since the CO concentration is low according to improvement of recent catalyst performance, the measurement apparatus body 2 having a long cell length and low concentration measurement range is used. Note that the measurement apparatus body 2 is not limited to absorption photometer typed one.

The control mechanism 3 is an electric circuit including, such as a CPU, a memory, an A/D converter, a D/A converter, and an amplifier (not shown), and it is configured that the CPU and the peripheral equipment thereof cooperate according to a program stored in the memory, and thus the control mechanism 3 controls the sampling mechanism 1 and performs a switching operation of the operation mode thereof.

Figure 2:
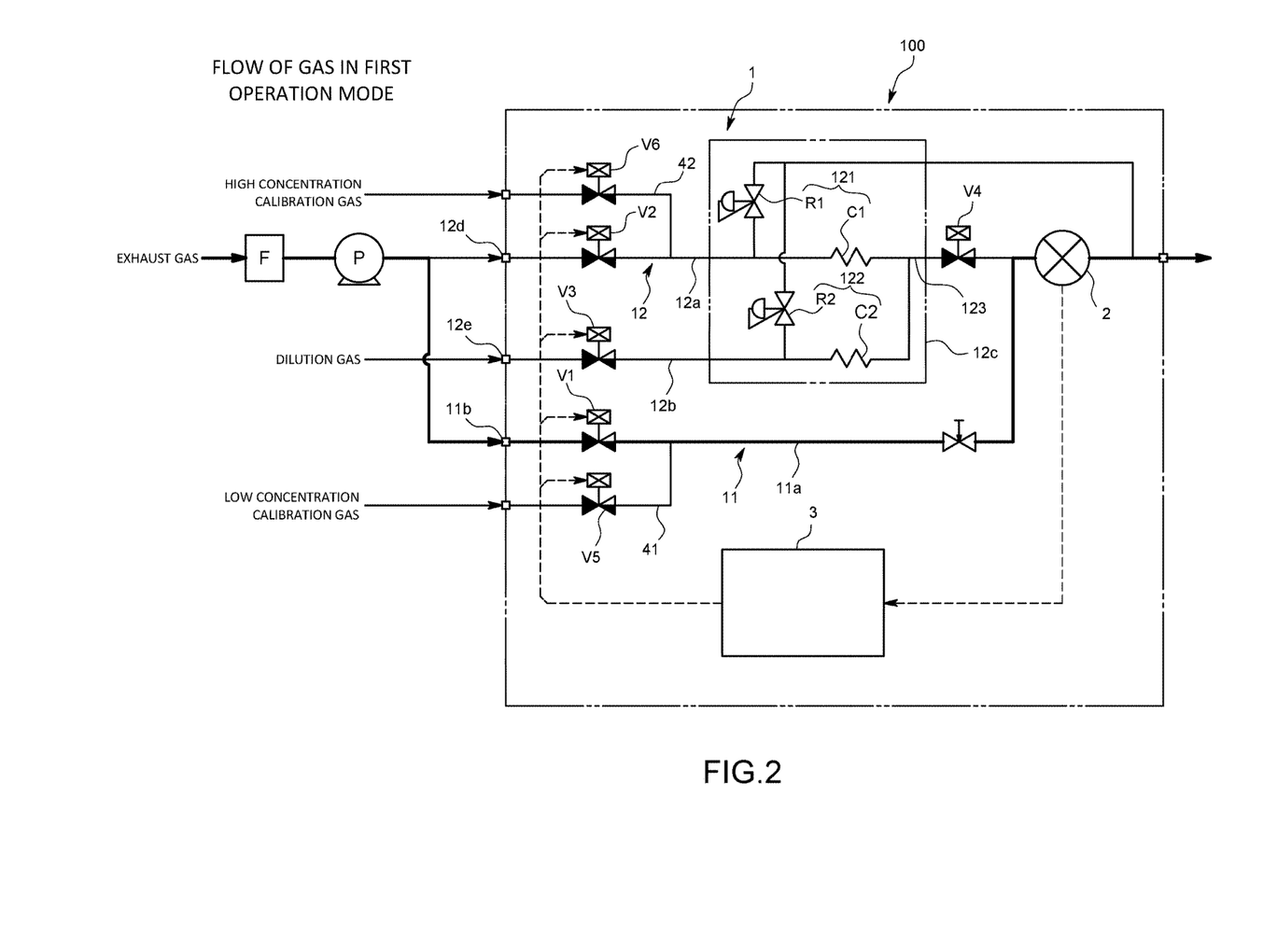
FIG. 2 is a fluid circuit diagram showing a flow of gas in a first operation mode of the exhaust gas measurement apparatus in the same embodiment.

Specifically, in the case where the sampling mechanism 1 is set in the first operation mode, the control mechanism 3 transmits an opening/closing signal to the sampling mechanism 1 to open the first valve V1 and simultaneously close the second valve V2 and the third valve V3. Alternatively, instead of closing the second valve V2 and the third valve V3, a fourth valve V4 provided on the pipe connecting between the mixing part 123 and the measurement apparatus body 2 may be closed. By this arrangement, as shown in FIG. 2, the sampling exhaust gas can be guided to the measurement apparatus body 2 without being diluted through the first flow channel system 11.

Figure 3:
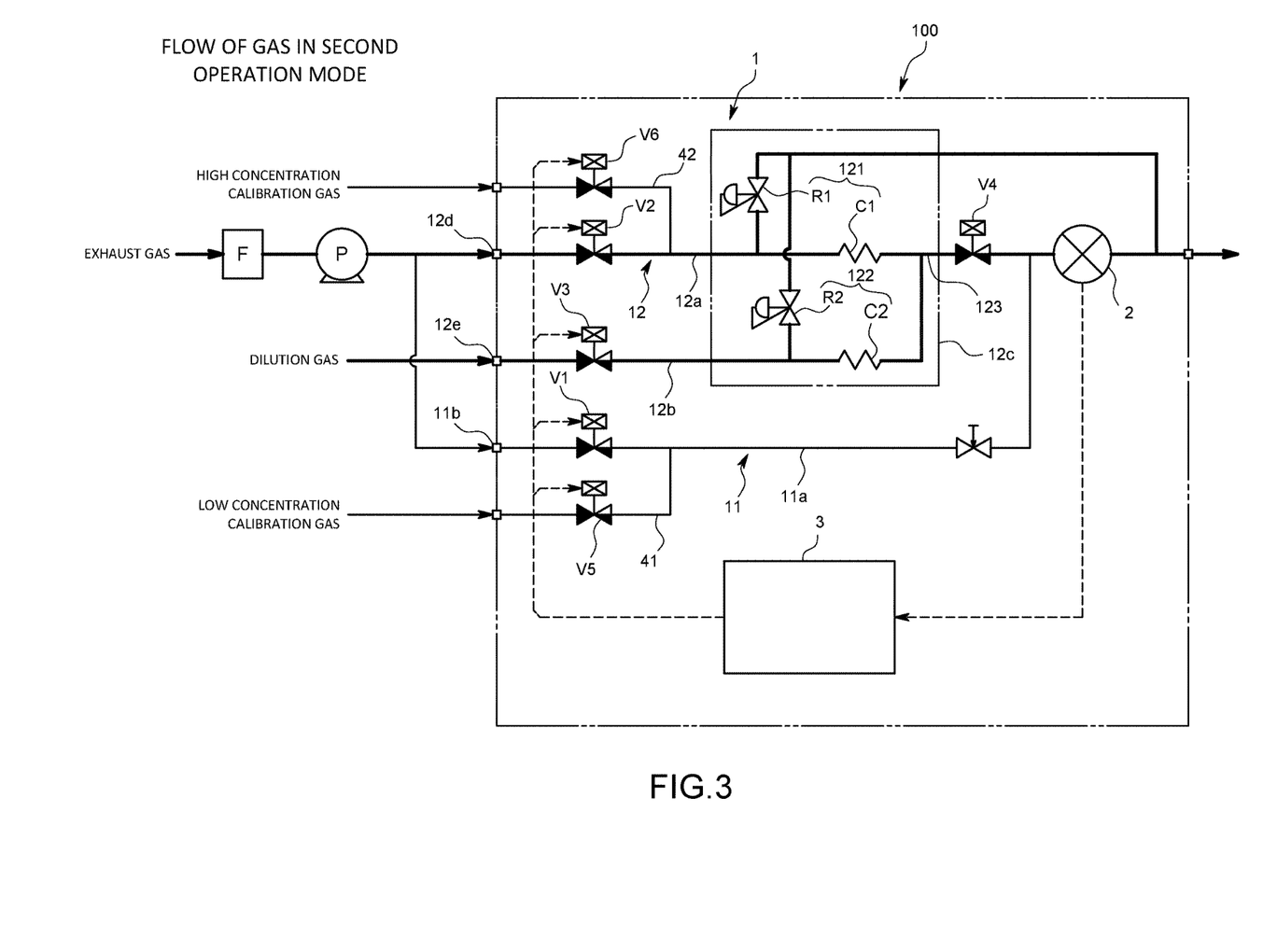
FIG. 3 is a fluid circuit diagram showing a flow of the gas in a second operation mode of the exhaust gas measurement apparatus in the same embodiment.

Meanwhile, in the case where the sampling mechanism 1 is set in the second operation mode, the control mechanism 3 transmits an opening/closing signal to the sampling mechanism 1 to open the second valve V2 and third valve V3 (together with the fourth valve 4) and simultaneously close the first valve V1. By this arrangement, as shown in FIG. 3, the sampling exhaust gas is guided to the second flow channel system 12 and diluted, and thus the diluted exhaust gas is guided to the measurement apparatus body 2. Next, the following describes a switching timing of the operation mode.

In the initial state, the sampling mechanism 1 is in the first operation mode. In this state, as shown in FIG. 2, undiluted sampling exhaust gas is guided to the measurement apparatus body 2 and the CO concentration is measured.

The control mechanism 3 receives the measurement data of the CO concentration transmitted from the measurement apparatus body 2 and monitors the value thereof.

Then in this first operation mode, for example, in the case where the concentration of the CO component contained in the sampling exhaust gas exceeds predetermined first threshold value such as in a state that the catalyst is not sufficiently warmed before the warming-up is completed, the control mechanism 3 switches the sampling mechanism 1 to be in the second operation mode. As a result, as shown in FIG. 3, the diluted sampling exhaust gas (i.e., mixture gas) is guided to the measurement apparatus body 2 and the concentration of the CO component contained in the mixture gas is measured. Note that the first threshold value is set to the measurable maximum value of the measurement apparatus body 2 or a value slightly smaller than the measurable maximum value.

Meanwhile, when the sampling mechanism 1 is in the state of the second operation mode, in the case where the catalyst warms up and the like and the function thereof is exerted, the concentration of the CO component contained in the sampling exhaust gas is lowered. Subsequently, when the concentration of the CO component contained in the mixture gas is lowered below a predetermined second threshold value, the control mechanism 3 switches the mode of the sampling mechanism 1 to the first operation mode. As a result, the undiluted sampling exhaust gas is guided to the measurement apparatus body 2 and the concentration of the CO component contained in the sampling exhaust gas is measured.

The second threshold value is set to measurable minimum value of the measurement apparatus body 2 or a slightly larger than the measurable minimum value.

In addition, in this embodiment, the sampling mechanism 1 is configured to be able to select a first calibration mode and a second calibration mode in addition to the first operation mode and second operation mode.

Figure 4:
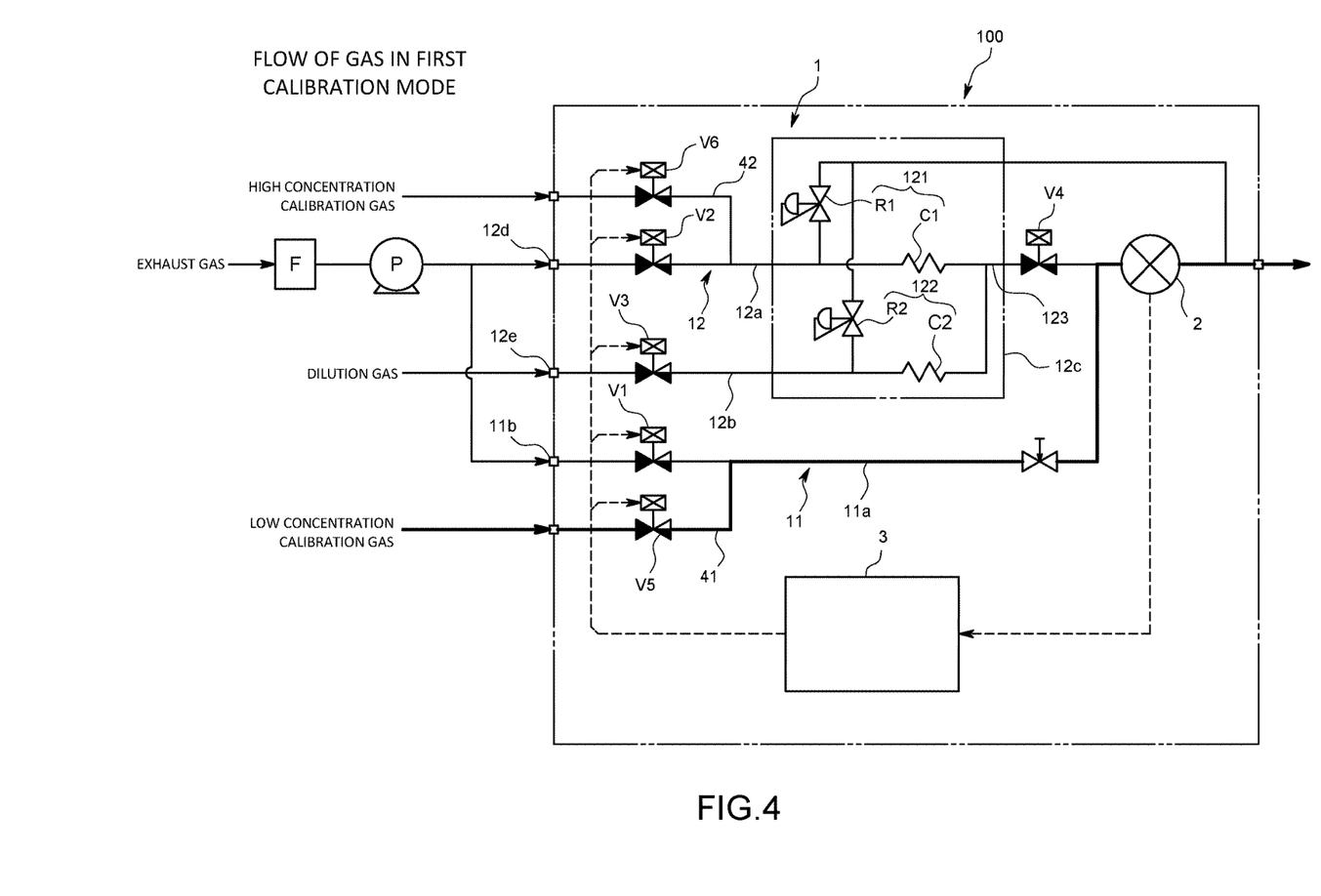
FIG. 4 is a fluid circuit diagram showing a flow of the gas in a first calibration mode of the exhaust gas measurement apparatus in the same embodiment.

In the first calibration mode, it is possible to calibrate the measurement concentration obtained in the first operation mode. For this purpose, a first calibration gas flow channel 41 for guiding calibration gas of a predetermined low CO concentration is connected to the middle of the first exhaust gas flow channel 11$a$ and a fifth valve V5 is provided in the middle of the first calibration gas flow channel 41.

In this first calibration mode, it is intended that, according to a command from the control mechanism 3, while the first valve V1 is closed, the fifth valve V5 is opened, and thus the low concentration calibration gas instead of the sampling exhaust gas is guided to the first exhaust gas flow channel 11$a$. The other operation is the same as that in the first operation mode.

Thus, it is intended that the low concentration calibration gas is introduced to the measurement apparatus body 2 and the measurement apparatus body 2 can be calibrated.

Figure 5:
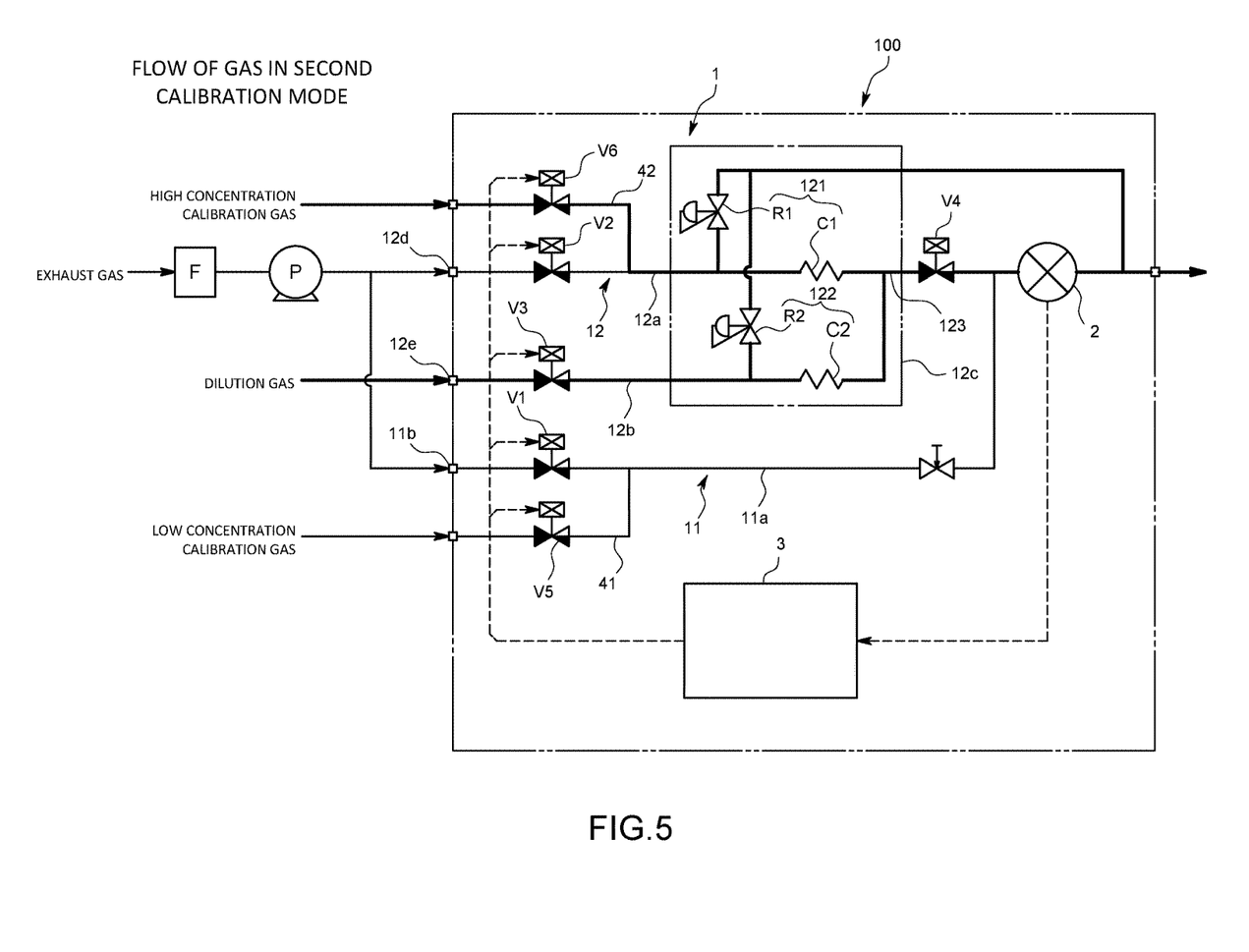
FIG. 5 is a fluid circuit diagram showing a flow of the gas in a second calibration mode of the exhaust gas measurement apparatus in the same embodiment.

In the second calibration mode, it is possible to calibrate the measurement concentration obtained in the second operation mode. For this purpose, a second calibration gas flow channel 42 for guiding calibration gas of a predetermined high CO concentration is connected to the middle of the second exhaust gas flow channel 12$a$ and a sixth valve V6 is provided in the middle of the second calibration gas flow channel 42.

In this second calibration mode, it is intended that, according to a command from the control mechanism 3, while the second valve V2 is closed, the sixth valve V6 is opened, and thus, as shown in FIG. 5, the high concentration calibration gas instead of the sampling exhaust gas is supplied to the second exhaust gas flow channel 12$a$. The other operation is the same as that in the second operation mode.

Thus, it is intended that the high concentration calibration gas is introduced to the measurement apparatus body 2 and the measurement apparatus body 2 can be calibrated.

Second Embodiment

In the first embodiment, although the flow channel systems are separated for the sampling exhaust gas to pass through in the first operation mode and in the second operation mode, respectively, it is also possible that, in the second operation mode, the dilution gas may be added and mixed to the sampling exhaust gas flowing in the first operation mode.

Figure 6:
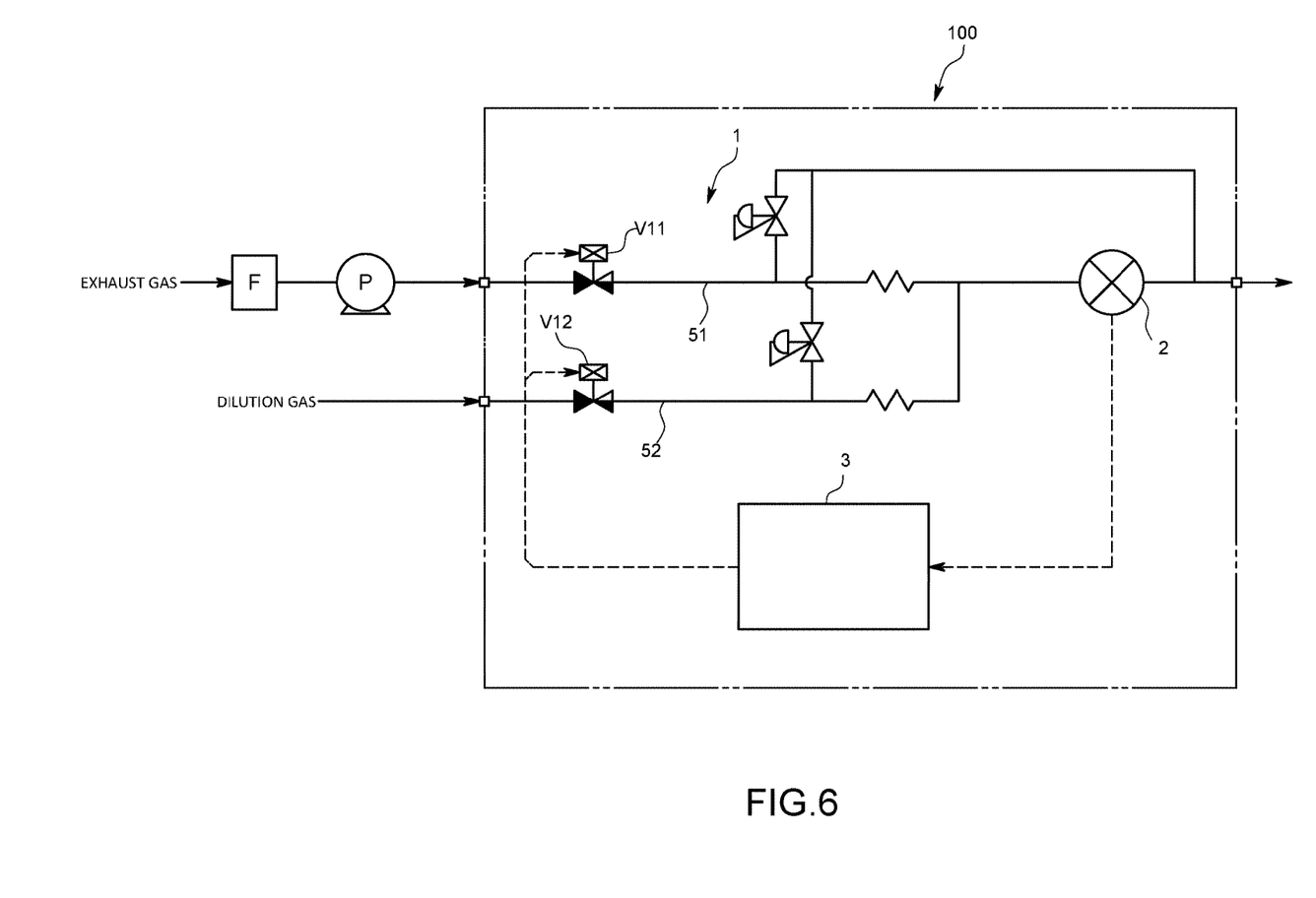
FIG. 6 is a fluid circuit diagram showing an entire exhaust gas measurement apparatus in a second embodiment of the present embodiment.

That is, as shown in FIG. 6, the exhaust gas measurement apparatus 100 according to the second embodiment is provided with a first exhaust gas flow channel 51 for introducing the sampling exhaust gas to the measurement apparatus body 2 and a dilution gas flow channel 52 which is connected to the middle of the first exhaust gas flow channel 51. Thus, in the first operation mode, according to a command from the control mechanism 3, while a valve V11 provided on the first exhaust gas flow channel 51 is opened, a valve 112 provided on the dilution gas flow channel 52 is closed, such that only the sampling exhaust gas is allowed to be guided to the measurement apparatus body 2. Meanwhile, in the second operation mode, the valve V12 provided on the dilution gas flow channel 52 is opened and mixture gas obtained by mixing the sampling exhaust gas and the dilution gas is allowed to be guided to the measurement apparatus body 2.

However, in this case, the flow rate of the gas guided to the measurement apparatus body 2 in the second operation mode becomes larger than that in the first operation mode only by an amount of the dilution gas, and there arises a significant difference in flow rate in the gas introduced to the measurement apparatus body 2 between in the first operation mode and in the second operation mode. Therefore, there may arise a difference in internal pressure of the cell and in subsequent back pressure thereafter, and it is liable cause a measurement error due to this difference. Conversely, in the first embodiment, since there is no significant difference in the flow rates of the gas introduced to the measurement apparatus body 2 either in the first operation mode or in the second operation mode, there is a merit that a malfunction such as a measurement error due to such a difference is hardly caused.

Further, in the exhaust gas measurement apparatus according to each of the first and second embodiments, the flow rates of the gas guided to the measurement apparatus body 2 are different and flow rate lengths to the measurement apparatus body 2 are different between in the first operation mode and in the second operation mode, there may possibly arise a difference in response time of the measurement apparatus body 2 when switching between the first operation mode and the second operation mode. As a method of making these response times coincident, the exhaust gas measurement apparatus may be configured that, a movement average time used for calculating measurement concentration is reduced to accelerate the response time for a mode of a slower response time when switching between the first operation mode and the second operation mode, or a waiting time is differently set according to a selected operation mode. Note that the present invention is not limited to the above embodiments.

Although the undiluted exhaust gas is guided to the measurement apparatus body in the first operation mode, the exhaust gas diluted at a dilution ratio lower than that in the second operation mode may be also guided to the measurement apparatus body.

In the first embodiment, gas is allowed to selectively flow only in one of the first flow channel system 11 or the second flow channel system 12. However, it may be also possible that, as shown in FIG. 7, while gas is allowed to simultaneously flow in the first flow channel system 11 (more specifically, in the first exhaust gas flow channel 11$a$) and in the second flow channel system 12 (more specifically, in the mixing part 123), either one of the gases flowing in the first and second flow channel systems 11 and 12 can be guided to the measurement apparatus body 2 and the other one of the gases is discharged to the outside of the exhaust gas measurement apparatus 100 immediately before the measurement apparatus body 2.

Figure 7:
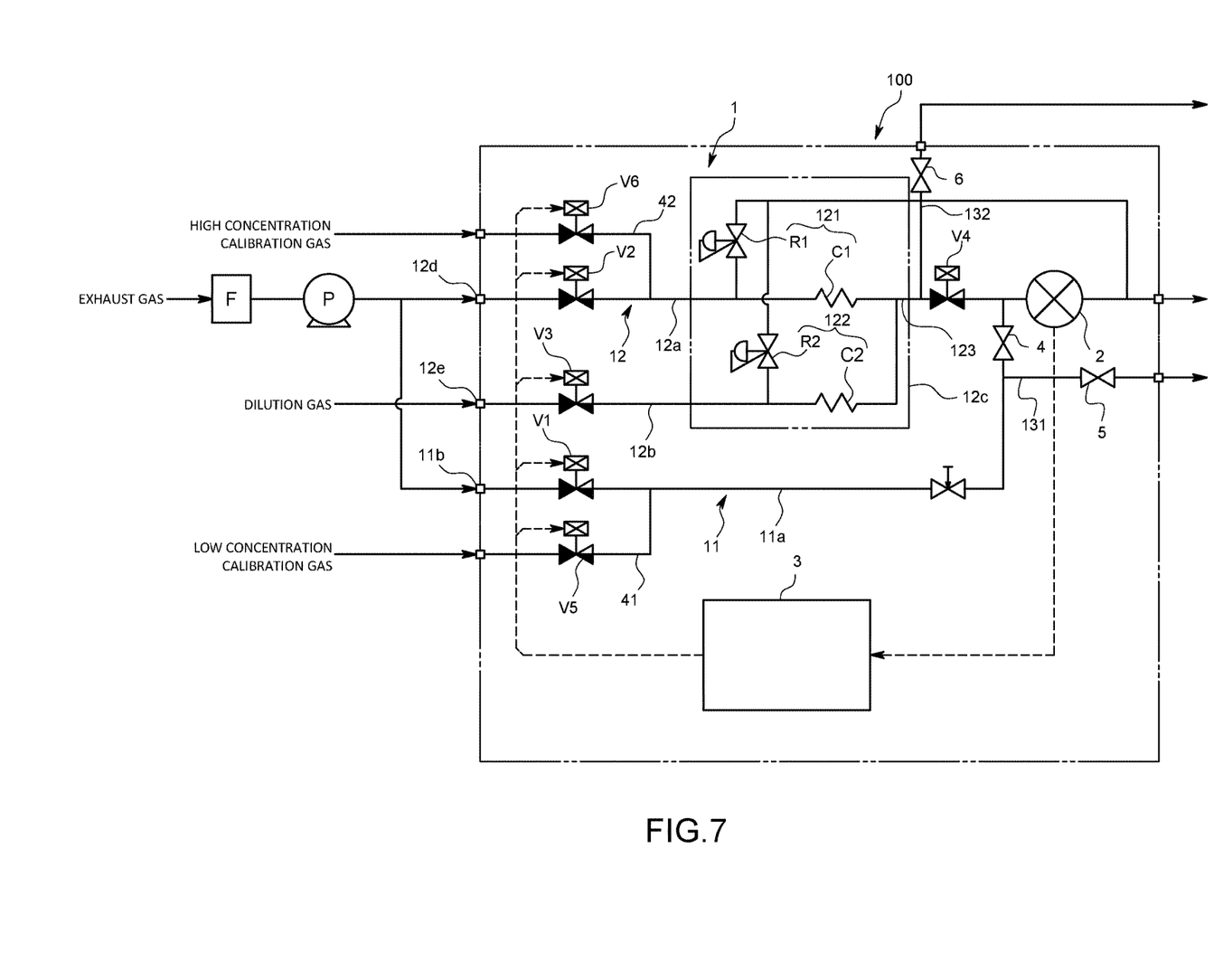
FIG. 7 is a fluid circuit diagram showing an entire exhaust gas measurement apparatus in the other embodiment of the present embodiment.

Therefore, the exhaust gas measurement apparatus 100 shown in FIG. 7 is configured to further include a first delivery channel 131 which is provided immediately before a junction to the mixing part 123 in the first exhaust gas flow channel 11a, and a second delivery channel 132 which is provided immediately before the fourth valve V4 in the mixing part 123. Note that, in FIG. 7, the members corresponding to those in the first embodiment are designated by the same reference signs.

A switching valve 4 is provided on the first exhaust gas flow channel 11a (more specifically, in the downstream side of the first delivery channel 131 in the first exhaust gas flow channel 11a) and another switching valve 5 is provided on the first delivery channel 131. Thus, by opening any one of the switching valves 4 and 5 while closing the other, the gas flowing in the first exhaust gas flow channel 11a is allowed to be switched whether the gas is discharged to the outside of the exhaust gas measurement apparatus 100 through the first delivery channel 131 or guided to the measurement apparatus body 2.

Meanwhile, further another switching valve 6 is provided on the second delivery channel 132. Thus, by opening any one of the switching valve 6 or the fourth valve V4 while closing the other, the gas flowing in the mixing part 123 is allowed to be switched whether the gas is discharged to the outside of the exhaust gas measurement apparatus 100 through the second delivery channel 132 or guided to the measurement apparatus body 2.

In this arrangement shown in FIG. 7, the first to third valves V1 to V3 are held in a normally opened state based on instructions from the control mechanism 3 in the operation mode.

Thus, in the first operation mode, based on the instructions from the control mechanism 3, by closing the switching valve 5 and opening the switching valve 4 while the fourth valve V4 is closed and the switching valve 6 is opened to thereby escape the mixture gas from the second delivery channel 132, the gas (exhaust gas) flowing in the first flow channel system 11 is allowed to be guided to the measurement apparatus body 2.

In the second operation mode, based on the instructions from the control mechanism 3, by opening the fourth valve V4 and closing the switching valve 6 while the switching valve 4 is closed and the switching valve 5 is opened to thereby escape the exhaust gas from the first delivery channel 131, the gas (mixture gas) flowing in the second flow channel system 12 is allowed to be guided to the measurement apparatus body 2.

With this configuration as described above, in either case of the first operation mode or the second operation mode, a portion in which the flow of the gas stops in the first flow channel system 11 and the second flow channel system 12 can be shortened. Therefore, when switching between the first operation mode and the second operation mode, the time until the flow of the gas from the first flow channel system 11 or the second flow channel system 12 is stabilized can be reduced.

In particular, in the second flow channel system 12, it is advantageous since the dilution ratio of the exhaust gas and the dilution gas can be kept stable before and after switching the operation mode.

In each of the embodiments, although the flow rate of the gas is constantly controlled using the pressure regulating valve and the fluid resistance element, the rates of the dilution gas and the sampling exhaust gas may be also controlled by a mass flow controller. Further, the dilution ratio may be also changed according to a type of an internal combustion engine or a testing condition.

A third operation mode or more operation modes may be provided to be able to change the dilution ratio in three steps or more.

In each of the embodiments, although the measurement concentration obtained in the first operation mode is calibrated according to the first calibration mode and the measurement concentration obtained in the second operation mode is calibrated according to the second calibration mode, it may be also possible to previously set a predetermined correlation coefficient between the measurement concentration in the first operation mode and the measurement concentration in the second operation mode to thereby calibrate the measurement concentration according to any one of the first and second calibration mode. Thus, it is also possible to calibrate the measurement concentration regarding the other operation mode using the correlation coefficient.

In this case, the correlation coefficient is to be stored in a predetermined region of the memory, and as an aspect of the correlation function, a numerical expression format or a table format may be also used.

Further, the low concentration calibration gas and the high concentration calibration gas may be supplied from separately prepared bombs, respectively, or only the high concentration calibration gas is prepared and the low concentration calibration gas may be adjusted by diluting the high concentration calibration gas.

In addition, various modifications and combinations of the components in the embodiments can be made without departing from the spirit of the present invention.

REFERENCE SIGNS LIST

100 . . . Exhaust gas measurement apparatus
. . . Sampling mechanism
. . . Measurement apparatus body
. . . Control mechanism

What is claimed is:
1. An exhaust gas measurement apparatus comprising:
   a sampling mechanism adapted to sample exhaust gas discharged from an internal combustion engine and to select and operate in any one of
      a lower dilution mode in which the sampled exhaust gas without dilution is output, or the sampled exhaust gas mixed with dilution gas of a predetermined ratio or less is output, and
      a higher dilution mode in which the sampling exhaust gas mixed with dilution gas greater than a predetermined ratio is output;
   a measurement apparatus body connected to the sampling mechanism and adapted to measure a concentration of a predetermined component contained in the gas introduced thereto; and
   a control mechanism adapted to,
      responsive to the concentration measured by the measurement apparatus body being less than a predetermined second threshold value and the sampling mechanism operating in the higher dilution mode, control the sampling mechanism to change from operating in the higher dilution mode to operating in the lower dilution mode, and responsive to the concentration measured by the measurement apparatus body exceeding a predetermined first threshold value and the sampling mechanism operating in the lower dilution mode, control the sampling mechanism to change from operating in the lower dilution mode to operating in the higher dilution mode.

2. The exhaust gas measurement apparatus according to claim 1, wherein flow rates of the sampling exhaust gas to be introduced to the measurement apparatus body are set to be different from each other in the lower dilution mode and the higher dilution mode, and the flow rate of the sampling exhaust gas in the lower dilution mode is set to be greater than the flow rate of the sampling exhaust gas in the higher dilution.

3. A recording medium that stores a program to be installed in an exhaust gas measurement apparatus that includes:
  a sampling mechanism adapted to sample exhaust gas discharged from an internal combustion engine and to select and operate in any one of
    a lower dilution mode in which the sampled exhaust gas without dilution is output, or the sampled exhaust gas mixed with dilution gas of a predetermined ratio or less is output, and
    a higher dilution mode in which the sampling exhaust gas mixed with dilution gas greater than a predetermined ratio is output,
  a measurement apparatus body connected to the sampling mechanism and adapted to measure a concentration of a predetermined component contained in the gas introduced thereto, and
  a control mechanism adapted to control the sampling mechanism, the program when executed by the exhaust gas measurement apparatus causes the control mechanism to exert functions of controlling the sampling mechanism
    to change from operating in the higher dilution mode to operating in the lower dilution mode responsive to the concentration measured by the measurement apparatus body being less than a predetermined second threshold value and the sampling mechanism operating in the higher dilution mode, and
    to change from operating in the lower dilution mode to operating in the higher dilution mode responsive to the concentration measured by the measurement apparatus body exceeding a predetermined first threshold value and the sampling mechanism operating in the lower dilution mode.

4. A control method of an exhaust gas measurement apparatus that includes
  a sampling mechanism adapted to sample exhaust gas discharged from an internal combustion engine and to select and operate in any one of
    a lower dilution mode in which the sampled exhaust gas without dilution is output, or the sampled exhaust gas mixed with dilution gas of a predetermined ratio or less is output, and
    a higher dilution mode in which the sampling exhaust gas mixed with dilution gas greater than a predetermined ratio is output; and
  a measurement apparatus body connected to the sampling mechanism and adapted to measure a concentration of a predetermined component contained in the gas introduced thereto, the method comprising:
  controlling the sampling mechanism to change from operating in the higher dilution mode to operating in the lower dilution mode responsive to the concentration measured by the measurement apparatus body being less than a predetermined second threshold value and the sampling mechanism operating in the higher dilution mode; and
  controlling the sampling mechanism to change from operating in the lower dilution mode to operating in the higher dilution mode responsive to the concentration measured by the measurement apparatus body exceeding a predetermined first threshold value and the sampling mechanism operating in the lower dilution mode.

* * * * *